United States Patent
Tabor

(10) Patent No.: US 11,823,458 B2
(45) Date of Patent: Nov. 21, 2023

(54) OBJECT DETECTION AND TRACKING SYSTEM

(71) Applicant: EMBEDTEK, LLC, Waukesha, WI (US)

(72) Inventor: Kent Tabor, Pewaukee, WI (US)

(73) Assignee: EMBEDTEK, LLC, Waukesha, WI (US)

( * ) Notice: Subject to any disclaimer, the term of this patent is extended or adjusted under 35 U.S.C. 154(b) by 0 days.

(21) Appl. No.: 17/351,987

(22) Filed: Jun. 18, 2021

(65) Prior Publication Data

US 2021/0397852 A1    Dec. 23, 2021

Related U.S. Application Data

(60) Provisional application No. 63/040,936, filed on Jun. 18, 2020.

(51) Int. Cl.
| | |
|---|---|
| *G06V 20/52* | (2022.01) |
| *H04N 5/33* | (2023.01) |
| *G01J 5/00* | (2022.01) |
| *G01J 5/60* | (2006.01) |
| *G06T 7/00* | (2017.01) |
| *G01J 5/48* | (2022.01) |
| *A61B 5/01* | (2006.01) |

(52) U.S. Cl.
CPC ............ *G06V 20/52* (2022.01); *G01J 5/0025* (2013.01); *G01J 5/60* (2013.01); *G06T 7/00* (2013.01); *H04N 5/33* (2013.01); *A61B 5/01* (2013.01); *G01J 5/48* (2013.01); *G01J 2005/0077* (2013.01); *G06T 2207/10024* (2013.01); *G06T 2207/10048* (2013.01)

(58) Field of Classification Search
None
See application file for complete search history.

(56) References Cited

U.S. PATENT DOCUMENTS

| | | | | |
|---|---|---|---|---|
| 4,027,159 A | * | 5/1977 | Bishop | G02B 23/12 |
| | | | | 250/342 |
| 5,836,398 A | | 11/1998 | White | |

(Continued)

FOREIGN PATENT DOCUMENTS

| | | |
|---|---|---|
| DE | 102018002955 A1 | 10/2018 |
| RU | 2352480 C1 | 4/2009 |

(Continued)

*Primary Examiner* — Stefan Gadomski
(74) *Attorney, Agent, or Firm* — Michael Best & Friedrich LLP

(57) ABSTRACT

An object detection and tracking system to identify an object of interest and to determine the location of the object within an area. The system includes a processing unit, a visual image system, a thermal image system, and a location mapping system. The visual image system is positioned relative to an area to capture a visual image of at least a portion of the area. The thermal image system is positioned relative to the area to capture a thermal image of at least a portion of the area concurrently with capture of the visual image to cooperatively identify an object in the area. The at least portion of the area captured in the thermal image conforms to the at least portion of the area captured in the visual image. The location mapping system is positioned relative to the area to determine a location of the object in the area.

9 Claims, 3 Drawing Sheets

(56) References Cited

U.S. PATENT DOCUMENTS

| | | | |
|---|---|---|---|
| 6,323,898 B1* | 11/2001 | Koyanagi | G01S 3/7864 |
| | | | 348/169 |
| 7,796,081 B2 | 9/2010 | Breed | |
| 7,924,146 B2 | 4/2011 | Seder et al. | |
| 8,411,245 B2 | 4/2013 | Lee et al. | |
| 8,692,739 B2 | 4/2014 | Mathieu et al. | |
| 9,037,343 B2 | 5/2015 | Aimura | |
| 9,312,605 B2 | 4/2016 | Sjölund | |
| 9,711,050 B2 | 7/2017 | Ansari | |
| 10,007,269 B1 | 6/2018 | Gray | |
| 10,055,979 B2 | 8/2018 | Stelzig et al. | |
| 10,169,680 B1* | 1/2019 | Sachdeva | G06T 7/174 |
| 10,210,401 B2 | 2/2019 | Allen et al. | |
| 10,220,852 B2 | 3/2019 | Valois | |
| 10,225,492 B1* | 3/2019 | Steffanson | H04N 5/33 |
| 10,274,958 B2 | 4/2019 | Delmarco et al. | |
| 10,275,797 B2 | 4/2019 | Freytag | |
| 10,496,911 B1* | 12/2019 | Walters | G06V 10/50 |
| 10,965,929 B1* | 3/2021 | Bellows | H04N 13/122 |
| 11,328,535 B1* | 5/2022 | Guo | G06V 20/647 |
| 2005/0264527 A1* | 12/2005 | Lin | G06F 3/011 |
| | | | 345/156 |
| 2007/0182818 A1* | 8/2007 | Buehler | G08B 13/19671 |
| | | | 348/143 |
| 2010/0157280 A1* | 6/2010 | Kusevic | G01S 7/4972 |
| | | | 356/4.01 |
| 2010/0231418 A1* | 9/2010 | Whitlow | G01S 17/86 |
| | | | 340/945 |
| 2011/0090343 A1* | 4/2011 | Alt | G06T 7/74 |
| | | | 348/E5.085 |
| 2011/0121159 A1* | 5/2011 | Mourar | G01S 17/86 |
| | | | 250/203.2 |
| 2012/0081544 A1* | 4/2012 | Wee | G01S 17/894 |
| | | | 348/140 |
| 2012/0274922 A1 | 11/2012 | Hodge | |
| 2014/0104432 A1* | 4/2014 | Lee | H04N 5/272 |
| | | | 348/143 |
| 2014/0132723 A1* | 5/2014 | More | G01S 7/497 |
| | | | 348/46 |
| 2015/0148077 A1* | 5/2015 | Jelle | H04W 4/022 |
| | | | 455/456.3 |
| 2015/0220789 A1* | 8/2015 | Wood | G06T 7/194 |
| | | | 382/103 |
| 2016/0202122 A1* | 7/2016 | Zhang | G01J 3/2823 |
| | | | 356/51 |
| 2017/0023945 A1* | 1/2017 | Cavalcanti | G08G 1/04 |
| 2018/0025234 A1 | 1/2018 | Myers et al. | |
| 2018/0067487 A1 | 3/2018 | Xu et al. | |
| 2018/0098727 A1* | 4/2018 | Spahn | G06T 7/0012 |
| 2018/0099663 A1 | 4/2018 | Diedrich et al. | |
| 2018/0101736 A1 | 4/2018 | Han et al. | |
| 2018/0129215 A1 | 5/2018 | Hazelton et al. | |
| 2018/0211121 A1 | 7/2018 | Moosaei et al. | |
| 2018/0211128 A1* | 7/2018 | Hotson | G06V 10/44 |
| 2018/0232947 A1* | 8/2018 | Nehmadi | G01S 7/295 |
| 2018/0233048 A1 | 8/2018 | Andersson et al. | |
| 2018/0341818 A1* | 11/2018 | Steffanson | G06T 7/001 |
| 2019/0071091 A1 | 3/2019 | Zhu et al. | |
| 2019/0095725 A1 | 3/2019 | Kalghatgi et al. | |
| 2019/0132709 A1* | 5/2019 | Graefe | G08G 1/096716 |
| 2019/0291723 A1* | 9/2019 | Srivatsa | G06K 9/627 |
| 2019/0387185 A1* | 12/2019 | Hicks | H04N 5/33 |
| 2020/0034657 A1* | 1/2020 | Yi | G06K 9/6261 |
| 2020/0146557 A1* | 5/2020 | Cheung | G06V 20/53 |
| 2020/0160030 A1* | 5/2020 | Lavi | G06T 17/05 |
| 2020/0265259 A1* | 8/2020 | Paul | G06V 20/58 |
| 2020/0327315 A1* | 10/2020 | Mullins | H04N 7/181 |
| 2020/0357143 A1* | 11/2020 | Chiu | G06V 10/454 |
| 2021/0012165 A1* | 1/2021 | Jiang | G06T 5/50 |
| 2021/0058605 A1* | 2/2021 | Lajevardi | H04N 5/332 |
| 2021/0062653 A1* | 3/2021 | Zeng | G06K 9/6257 |
| 2021/0158501 A1* | 5/2021 | Bhat | G06N 3/02 |
| 2021/0181758 A1* | 6/2021 | Das | G06V 10/25 |
| 2021/0211831 A1* | 7/2021 | Gan | G06K 19/07758 |
| 2021/0219869 A1* | 7/2021 | Ryu | A61B 5/1073 |
| 2021/0256747 A1* | 8/2021 | Ryu | H04N 5/23229 |
| 2021/0263525 A1* | 8/2021 | Das | G06T 7/246 |
| 2021/0287469 A1* | 9/2021 | Ryhorchuk | G06V 40/172 |
| 2021/0295530 A1* | 9/2021 | Janjic | G06T 7/20 |
| 2022/0005332 A1* | 1/2022 | Metzler | G08B 13/1965 |
| 2022/0058811 A1* | 2/2022 | Pokhrel | G06T 7/215 |
| 2022/0094883 A1* | 3/2022 | Jia | H04N 5/33 |
| 2022/0169381 A1* | 6/2022 | Alrasheed | G05D 1/0094 |

FOREIGN PATENT DOCUMENTS

| | | |
|---|---|---|
| WO | 2017138866 A1 | 8/2017 |
| WO | 2018196000 A1 | 10/2018 |

* cited by examiner

OBJECT DETECTION AND TRACKING SYSTEM

CROSS-REFERENCE TO RELATED APPLICATIONS

This application claims priority to U.S. Provisional Patent Application No. 63/040,936, filed on Jun. 18, 2020, and entitled "Object Detection and Tracking System," the contents of each of which is hereby incorporated by reference in its entirety.

BACKGROUND

The present invention relates to an object detection and tracking system to identify and determine the location of objects in an area, and more particularly to an object detection system including different sensor systems to detect objects in the area.

Many existing object detection systems include cameras to identify objects (e.g., humans, animals, etc.) moving through or in an area. Some other systems include a thermal sensor system or a motion detection system to identify the presence of an object in an area. But thermal sensor systems and motion detection systems are limited in their ability to identify what the object is or accurately determine the object's location. In addition, existing systems often falsely identify the objects to be identified, or miss objects entirely. For object detection systems with a camera, these failures can be attributed to viewing limitations of the camera when trying to detect, identify, or determine the position of an object. In addition, camera systems alone cannot determine an accurate location of people in an area when a person's physical size is used for an estimation of their location due to the wide variability in human height and size. Existing systems also tend to be complicated to install, calibrate, and update as the environment changes (e.g., when machinery or equipment is moved around).

SUMMARY

The invention provides an object detection and tracking system that detects objects in an area using, in one example, a visual image sensor system, a thermal sensor system, and an object location mapping system or location mapping system (e.g., a three-dimensional (3D) mapping or identification system). The object detection system is constructed identify, determine the position, and track an object with a thermal heat range that is consistent with the thermal heat range of a human. The object detection and tracking system may automatically define and adapt to a work space of the area being monitored.

In one aspect, the invention provides an object detection and tracking system including a visual image system that captures one or more visual images of an area, and a thermal image system that captures one or more thermal images of the area concurrently with the visual image system capturing the visual image(s). The thermal image system detects a thermal signature of an object in the area, and the visual image system and the thermal image system cooperate to determine that the object is the same in the visual image and in the thermal image. The systems also identify the object as being different from the thermal background in the thermal image. The object detection and tracking system also includes a location mapping system that determines a location of the object in the area. The visual image system, the thermal image system, and the location mapping system facilitate identification of the object and tracking of the object in the area. The coordinated use of the visual image and the thermal image for the same object makes determining the location of the object substantially more reliable and consistent. The addition of LIDAR, 3D cameras (including time-of-flight type cameras), 3D stereo cameras, other types of 3D sensor imaging, or other point cloud methods make determining the object's location very accurate regardless of the object's specific shape.

In another aspect, the invention provides an object detection and tracking system including a visual image system positioned relative to an area to capture a visual image of at least a portion of the area and a thermal image system positioned relative to the area to capture a thermal image of at least a portion of the area concurrently with capture of the visual image to cooperatively identify an object in the area having a thermal signature. The at least portion of the area captured in the thermal image conforming to the at least portion of the area captured in the visual image. A location mapping system is positioned relative to the area to determine a location of the object in the area.

In another aspect, the invention provides an object detection and tracking system including a visual image system positioned relative to an area to capture a visual image of at least a portion of the area, a thermal image system positioned relative to the area to capture a thermal image of at least a portion of the area, and a location mapping system is positioned to determine a working space of the area (e.g., in 3D). The working space defined by one or more portions of the area that are unobstructed by one or more inanimate objects relative to a first viewpoint of the visual image system and a second viewpoint of the thermal image system. The location mapping system generates a map of the working space of the area.

Figure 1:
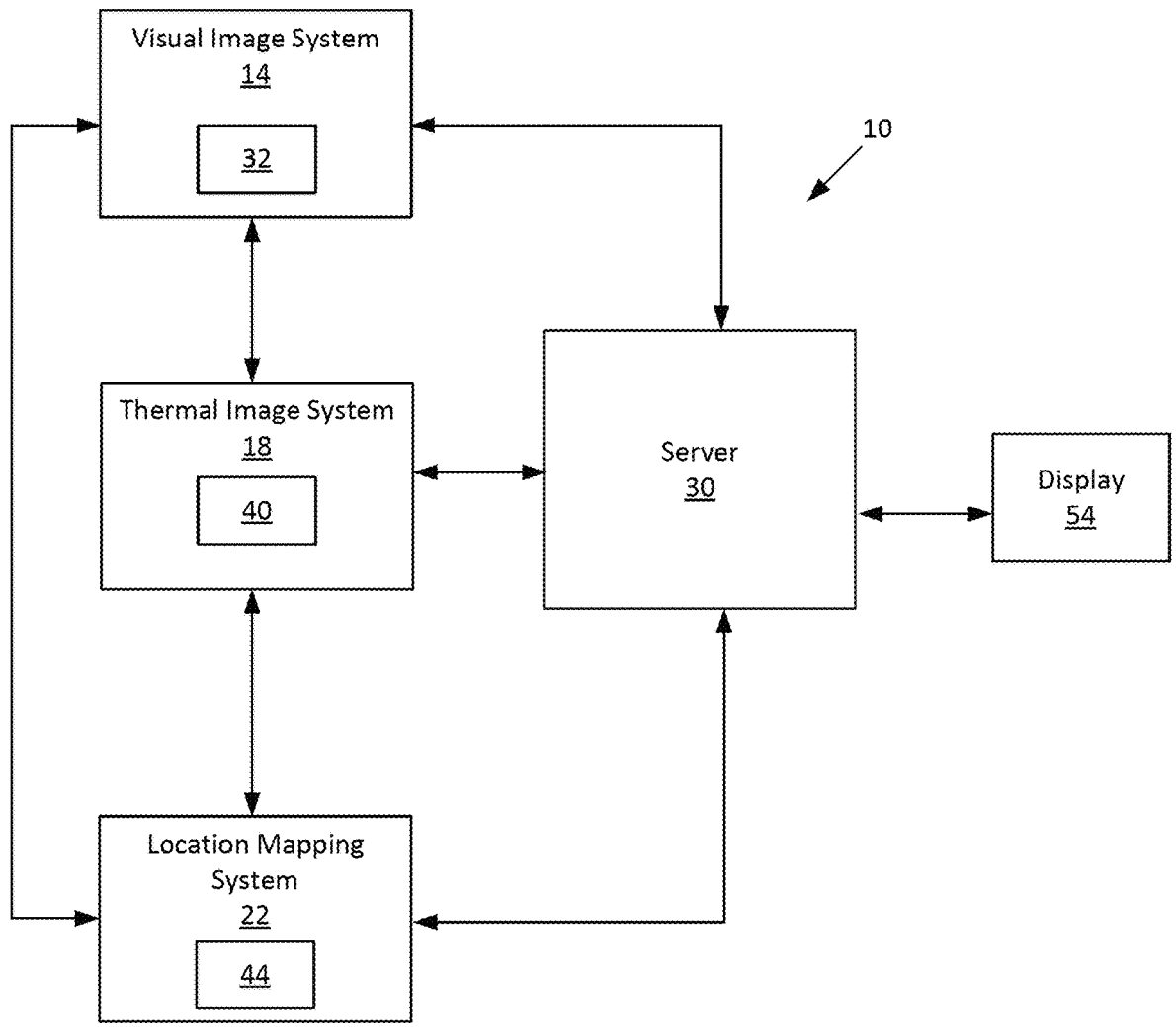
FIG. 1 is a schematic view of an exemplary object detection and tracking system of the present invention including a visual image system, a thermal image system, and a location mapping system that communicate with each other and with a processor and/or a server.

Before any embodiments of the present invention are explained in detail, it should be understood that the invention is not limited in its application to the details or construction and the arrangement of components as set forth in the following description or as illustrated in the drawings. The invention is capable of other embodiments and of being practiced or of being carried out in various ways. It should be understood that the description of specific embodiments is not intended to limit the disclosure from covering all modifications, equivalents, and alternatives falling within the spirit and scope of the disclosure. Also, it is to be understood that the phraseology and terminology used herein is for the purpose of description and should not be regarded as limiting.

DETAILED DESCRIPTION

Figure 2:
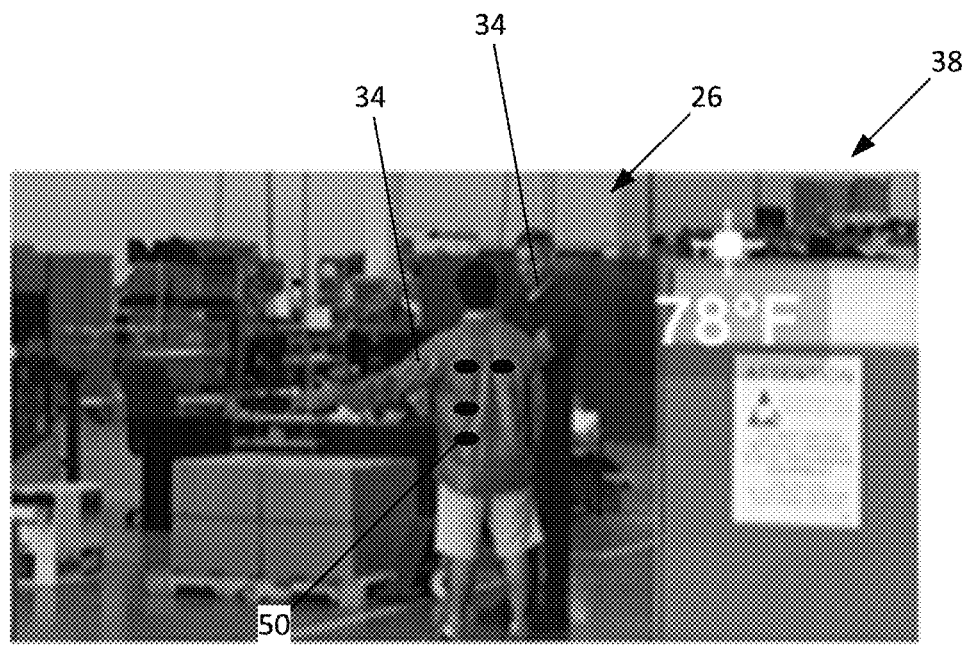
FIG. 2 is an exemplary visual image of an area that is captured by the visual image system of FIG. 1 and that is analyzed by the location mapping system
Figure 3:
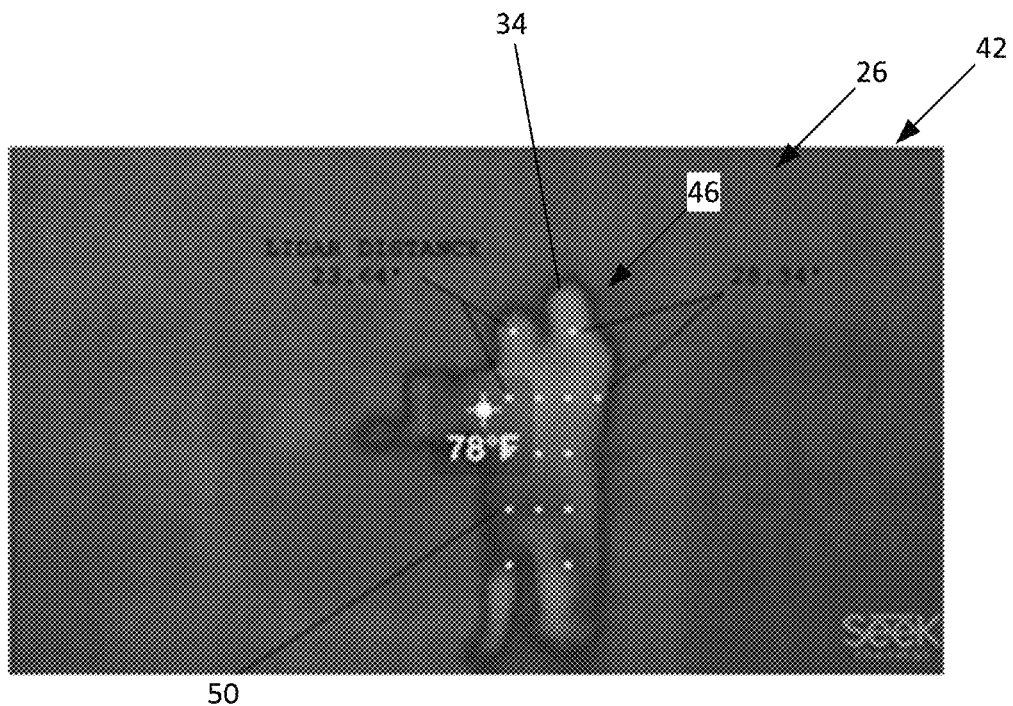
FIG. 3 is an exemplary thermal image of the area of FIG. 2 captured by the thermal image system of FIG. 1, and location information determined by the location mapping system of FIG. 1.

FIG. 1-3 illustrate an exemplary object detection and tracking system 10 ("ODT system 10" for ease of reference) including a visual image system 14, a thermal image system 18, and a location mapping system 22 that are positioned to monitor a three-dimensional (3D) area 26 (e.g., a facility, a warehouse, etc.) to determine a location of one or more objects (e.g., a person) and/or the identity of the object(s) in the area 26. With reference to FIG. 1, the visual image system 14, the thermal image system 18, and the location mapping system 22 communicate (e.g., wired or wireless, or a combination of wired and wireless) with each other and with a server or processing unit 30 (e.g., having any one or a combination of a microprocessor, a processing chip, storage, etc.). It should be appreciated that each of the visual image system 14, the thermal image system 18, and the location mapping system 22 may only communicate with the processing unit 30, that fewer than all of the systems 14, 18, 22 may only communicate with the processing unit 30 (e.g., one or more of the systems 14, 18, 22 may only communicate with another of the systems 14, 18, 22), or that two of the systems 14, 18, 22, may communicate with each other and the processing unit 30 while the remaining system may only communicate with the processing unit 30. In some constructions, one or more of the systems 14, 18, 22 may communicate with one or more of the other systems 14, 18, 22 via (e.g., through) the processing unit 30. Other variations of communication between the systems 14, 18, 22, and between the systems 14, 18, 22 and the processing unit 30 are possible and considered herein.

With reference to FIGS. 1 and 2, the visual image system 14 includes one or more optical sensors 32 (e.g., as part of a camera) to optically capture an image of at least a portion of the area 26 that may include object(s) 34 that are desired to be detected. It will be appreciated that the visual image system 14 can dynamically capture images 38 of the area 26 (e.g., in the form of multiple images or a video; for the purposes of description and the claims, the term 'image' shall refer to either a static image or a video). In some embodiments, the image 38 may be store in the visual image system 14 or the processing unit 30 (e.g., recorded). In other embodiments, the image 38 may be analyzed only by the ODT system 10 (e.g., the image 38 is not stored or recorded in the visual image system 14). As shown in the exemplary illustration in FIG. 2, the visual image system 14 captures a visual image 38 of a portion of the area 26 (e.g., triggered by motion detection in the area 26) that includes inanimate objects or elements (boxes, pallets, equipment, etc.) and living objects 34 (e.g., people to be tracked and/or identified in the illustrated image 38).

The thermal image system 18 (e.g., an infrared image system, mid infrared or "MIR", or far infrared or "FIR", etc.) facilitates identification of the objects 34 and works simultaneously or concurrently with the visual image system 14 to do so. More specifically, the thermal image system 18 captures a thermal image 42 of the same or a similar portion of the area 26 that is captured by the visual image system 14. For example, the visual image system 14 may have a first viewpoint to capture the visual image 38 of at least a portion of the area 26 and the thermal image system 18 may have a second viewpoint to capture the thermal image 42 conforming to the at least portion of the area 26. In other words, the visual image 38 and the thermal image 42 might have slightly different extents (e.g., left/right, top/bottom borders of the captured images 38, 42), but visual and thermal images 38, 42 each capture generally the same portion of the area 26.

The thermal image system 18 includes one or more thermal sensors 40 that detect thermal attributes of objects 34 (e.g., via the thermal signature associated with the objects 34) that are in the area 26. For purposes of the description and the claims, the term "thermal object" refers to an object that has thermal attributes or a thermal signature that falls within a predefined thermal heat range. Also for purposes of the description and the claims, the term "object of interest" may be the thermal object. For example, mammals typically have thermal heat signatures from a range from 97° F. to 105° F., birds have thermal heat signatures of approximately 105° F., and cold blooded animals have thermal heat signatures in a range from 50° F. to approximately 100° F. In addition, vehicles may include motors or engines that operate in a range from the approximately 100° F. to 200° F., or even higher. As a result, the predefined thermal range may be in a range from 50° F. to 200° F. to detect any thermal object from cold-blooded animals to vehicles. In some constructions, the predefined thermal range may be from 90° F. to 200° F. to detect mammals, birds, and vehicles. In other constructions, the predefined thermal range may be from 70° F. to 150° F. to ensure that mammals (e.g., people) with thermally-insulating clothing and vehicles can be detected. The ODT system 10 may determine the type of thermal object that is detected based on the thermal signature when the signature is compared to the predefined thermal range. In some constructions, the ODT system 10 may determine, via the processing unit 30, whether a thermal signature of the object 34 differs relative to background in the thermal image based on a comparison of a color of the thermal signature relative to a color of the background, or some other comparison of the object 34 relative to the background of the thermal image. When the thermal signature of the object 34 differs relative to the background, the ODT system 108 communicates with the visual image system 14 and the location mapping system to facilitate identifying and locating the object.

Although the example described in detail and illustrated in the Figures is focused on the objects as people, it will be appreciated that the thermal object(s) 34 may include other mammals or operating equipment (e.g., vehicles). In addition, it should be appreciated that the thermal object 34 may be only a portion of a person (e.g., a head, leg, arm, etc.) or a portion of another thermal object. In general, the ODT system 10 identifies the object of interest by differentiating the object from the visual background in the visual image and from the thermal background in the thermal image. The processing unit 30, or another controller or processor of the system 10, communicates with the visual image system and the location mapping system to facilitate identifying and locating the object when the thermal signature of the object is within the predefined thermal heat range or when the heat signature of the object 34 is differentiated relative to the background of the thermal image.

The location mapping system 22 (e.g., Light Detection and Ranging ("LiDAR"), 3D camera technology, stereo camera technology, or other 3D imaging or mapping technology) determines a location or position of the objects in the area 26, including objects 34, on an X-Y map of the area 26 using one or more light sensors 44 (e.g., pulsed lasers 50). The light sensor 44 determines the distance to the objects from the position of the location mapping system 22 (e.g., in the same vicinity as the systems 14, 18). By determining the location of the objects 34 and other objects in the area 26, as well as portions of the area 26 without any objects, the location mapping system 22 utilizes information from the light sensors 44 to generate an X-Y map of the working space (e.g., where people can move about) of the area 26 and the location of inanimate objects (e.g., objects not of interest). The location mapping system 22 can define the working space prior to or concurrent with determining a location of an object 34 in the area 26.

As shown in FIG. 1, the visual image 38, the thermal image 42, and the information or signals from the light sensors 44 are transmitted to the processing unit 30. The processing unit 30 processes the images 38, 42 using background subtraction to separate the inanimate elements (e.g., the boxes and pallets) from the animate elements and objects 34 (e.g., the people in the illustrated example). Background subtraction of the thermal image 42 can be accomplished by comparing the thermal signature of one or more objects 34 relative to the background of the thermal image 42. The processing unit 30 also locates the precise position of the objects 34 on the X-Y map based on the information from the light sensors 44. In some constructions, one or more of the systems 14, 18, 22 may directly process the images 38, 42 and/or the location information (e.g., when a processing unit 30 is not provided in the ODT system 10, or in addition to the ODT system 10 having a processing unit) depending on the functionality of the systems 14, 18, 22.

In general, the visual image system 14 does not require a high resolution optical sensor 32 to independently identify objects in the area 26, and the thermal image system 18 does not require high resolution to identify objects based on their thermal image. Instead, the two systems 14, 18 work together to more precisely identify the object(s) 34 to be tracked. More specifically, the ODT system 10 uses the signals and data from the visual image system 14 and the thermal image system 18 to determine whether a thermal object (e.g., the people 34) that is in a particular location in the visual image 38 is also in the same or similar location in the thermal image 42. If so, the ODT system 10 identifies the object as a thermal object 34 to be tracked in the area 26. For example, when the thermal image system 18 detects the heat signature of the thermal object 34 is within the predefined thermal heat range, the thermal image system 18 may communicate with the visual image system 14 and the location mapping system 22 to facilitate identification of the thermal object. That is, the ODT system 10 compares the position of the thermal object 34 in the visual image 38 to the position of the thermal object 34 in the thermal image 42. If the positions in each image 38, 42 are the same or substantially the same (e.g., the object 34 in the visual image 38 coincides with the object in the thermal image 42), the ODT system 10 determines that the visual profile of the thermal object 34 in the visual image and the thermal object 34 are the same object and is tracked by the system 10.

The ODT system 10 also leverages the information or signals from the location mapping system 22 (via the sensor(s) 44) to detect the precise position of the object 34 on the X-Y map based on the identification of the object 34 that is identified by the visual image system 14 and the thermal image system 18. Because the visual image system 14 and the thermal image system 18 cooperatively identify the object(s) 34, the location mapping system 22 does not require a high resolution to separately or independently identify the object by shape, size, or thermal signature. The ODT system 10 overlays the cooperative information from each of the three independent systems 14, 18, 22 to identify an object 34, locate the object 34, and track the object 34. For example, when the identification information from the visual image system 14 and the thermal image system 18 are used with the 3D location information of the object 34 to be tracked from the location mapping system 22, the Y-location on the X-Y map of the image being analyzed can be used to determine the precise location or position of the object in the 3D area 26. The Y-location information may be helpful when tracking a person who is wearing thermally-insulated clothing or footwear, which can make thermal detection of the person more difficult. In some constructions, the ODT system 10 may alert personnel or equipment in the area 26 (e.g., via the processing unit 30) that an object 34 is in the area 26, and provide the location of the object 34, even when the object 34 is moving.

The ODT system 10 can dynamically capture images 38 or record a video of the area 26 so that personnel can actively view or monitor the area 26 relative to equipment that may be operating in the area 26 to inhibit adverse interactions between the equipment and the object(s) being monitored. It will be appreciated that the captured images 38 may be analyzed by the ODT system 10 for real-time pedestrian detection (e.g., to determine potential or real collisions with equipment or other objects, for security purposes, etc.). For example, when a person 34 is in the area 26, the ODT system 10 may send a signal to the equipment or other personnel that the person 34 and the equipment may collide. In the illustrated construction, the signal may be sent by the processing unit 30 via an output 54 (e.g., a wireless output or alarm on equipment). The ODT system 10 may also alert personnel monitoring the area 26 that a person or other object 34 is in the area 26 (e.g., when the person is not supposed to be in the area 26). In some constructions, the visual image system 14, the thermal image system 18, and the location mapping system 22 may communicate with the processing unit 30 to analyze and store (e.g., via a cloud based storage system) the images or video, including the processed images 38, 42 and information. The output 54 may include a display (e.g., a computer, a mobile device, etc.) that allows a user to view the processed information (including the image 38, the image 42, and the information from the sensor(s) 44). In some constructions, the output 54 may perform other functions (e.g., tie an identification or location signal to an alarm, warning, or alert system (e.g., on a fork lift).

Figure 4:
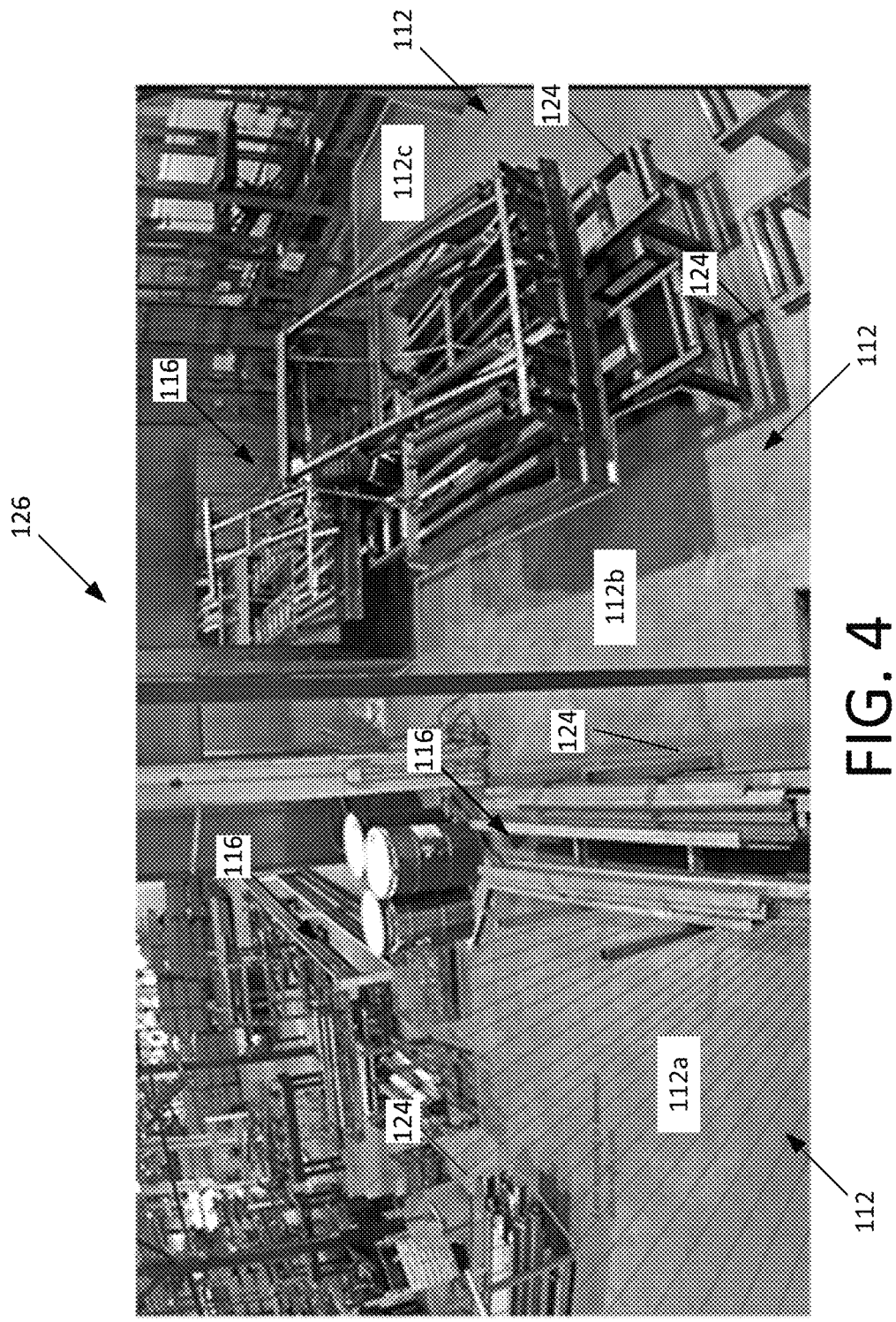
FIG. 4 is an exemplary area that is monitored by the object detection and tracking system and that is mapped on a 3D X-Y map by the location mapping system to determine active zones and blind zones in the field of view.

FIG. 4 illustrates that the ODT system 10 implements the location mapping system 22 determine a working space 112 of an area 126 (i.e. the space in which personnel can move about). For example, the location mapping system 22 may communicate with the visual image system 14 and the thermal image system 18 to determine the working space 112 of the area 126. The ODT system 10 leverages the information or signals from the location mapping system 22 (via the sensor(s) 44) to detect the precise position of objects and the working space 112 on the X-Y map. In the illustrated construction, the area 126 is part of a warehouse that includes inanimate elements 116 (e.g., machinery, materials, racking, etc.) that obscures the optical and thermal vision of the ODT system 10. The location mapping system 22 determines the open and/or working space 112 in the area 126 (using coordinates on an X-Y map generated by the system) and excludes portions of the area 126 that extend above the floor or working space. For example, the working space 112 is defined as one or more portions of the area 126 that are unobstructed by one or more inanimate objects 116 relative to a first viewpoint of the visual image system 14 and a second viewpoint of the thermal image system 18 and that may be traversed by a person or a vehicle normally (i.e. without climbing onto or over inanimate object(s) 116). The ODT system 10 automatically defines the working space 112 with a geofence 124 that is generated by the location mapping system 22, and can dynamically adjust the working space 112 and the related geofence 124 when inanimate object(s) 116 are moved. The geofence 124 may be used to auto-create a facility map that indicates portions of the area 126 that overlap (e.g., portions that are monitored by one or more of the systems 14, 18, 22) and portions of the area 126 that are dead or blind zones (e.g., portions that cannot be monitored by any system 14, 18, 22 due to obstructions of the inanimate object(s)). The facility map allows the ODT system 10 to determine the percentage of the area 126 that is considered a working space 112 and the percentage (and location) of any blind zones within the area 126 to compensate for the blind zones. In some constructions, the working space 112 may be a continuous portion, or segmented (i.e. non-continuous) portions of the area 126 that form working space zones 112a, 112b, 112c. The working space 112 may include or encompass a part of the area 126, or the entire area 126. In other words, the working space 112 may be a small portion of the overall area 126 or the entirety of the area 126 (when no obstructions or inanimate objects 116 exist in the area 126).

The facility map created by the ODT system 10 allows for predictive tracking data to be collected because the object(s) may move in or between one or more of the first workspace zone 112a, the second workspace zone 112b, and the third workspace zone 112c. As shown in FIG. 4, the zones 112a, 112b, 112 are separated by blind zones (e.g., defined by pallets or obscured portions of the area 126 relative to the ODT system 10). As a result, when the object 34 being tracked moves to or through a blind zone, the ODT system 10 may predict the next location or position of the object 34 in the area 126 based on the working space 112 that is defined by the location mapping system 22. For example, when the object of interest is in or enters a blind zone of the area 126 (e.g., between the first and second workspace zones 112a, 112b), the ODT system 10 predicts a next position of the object in the area 126.

The working space 112 may change due to the inanimate objects 116 being maneuvered in the area 126 during typical work flow within the area 126. As a result, the ODT system(s) 10 may automatically adjust the working space 112 when any changes within the area 126 occur. For example, a temporary load of stacked pallets may be positioned in a spot that blocks some or all of the systems 14, 18, 22 ODT system 10. The ODT system 10 may determine the area behind the pallets is a blind zone and use the adjusted working space 112 to predict the next location of an object to be tracked. By dynamically determining the working space 112, the ODT system 10 uses the images and information from the visual image system 14, the thermal image system 18, and the location mapping system 22 to identify and track objects 34 in the working space 112.

It should be appreciated that the ODT system 10 can be implemented as a self-learning and an adaptive system that updates the working space 112 based on movement of objects within the area 26 (e.g., for real time or near-real time monitoring of the area 26). The visual image system 14 and the thermal image system 18 are visual systems that use background detection and edge detection, and that produce images that are analyzed to determine whether an object is an object of interest. The location mapping system 22 then provides information regarding the location of the object of interest from the place where the system 22 is implemented (e.g., a distance from the sensor(s) 44 to the object of interest). In this way, the ODT system 10 provides a map so that after the system 10 determines that the object is an object 34 to be tracked, the location of the object 34 can be accurately determined within the XY map. The location mapping system 22 informs where all objects and physical boundaries are located within the area 26, including the floor, walls, and any objects (e.g., racking or shelves, etc.) on or above the floor. This 3D mapping can be accomplished by using LIDAR, 3D cameras, sound, or radar, or stereo camera technology. The system can auto calibrate and auto setup the XY floor map and adapt as the area 26 changes. In this way, the ODT system 10 can intelligently scan the floor and determine active tracking areas as well as blind areas within the space being monitored.

While the example described in detail herein relates to monitoring a warehouse or manufacturing facility, and aspects related to a warehouse or manufacturing facility, it should be appreciated that the ODT system 10 may be used to monitor any area 26, 126. By combining 3D mapping characteristics, with optical and thermal imaging, the system can be automatically set up and can easily adapt to changes in the area that is being monitored.

The embodiment(s) described above and illustrated in the figures are presented by way of example only and are not intended as a limitation upon the concepts and principles of the present disclosure. As such, it will be appreciated that variations and modifications to the elements and their configurations and/or arrangement exist within the scope of one or more independent aspects as described.

The invention claimed is:

1. A system comprising:
a visual image system including one or more optical sensors positioned relative to an area to capture a visual image of at least a portion of the area;
a thermal image system including one or more infrared sensors positioned relative to the area to capture a thermal image of at least a portion of the area; and
a location mapping system including one or more sensors positioned to determine a working space of the area, the location mapping system configured to communicate with the visual image system and the thermal image system to determine one or more blind zones of the area that are obstructed by one or more inanimate objects, the working space defined by one or more portions of the area that are unobstructed by one or more inanimate objects relative to one or both of a first viewpoint of the visual image system and a second viewpoint of the thermal image system;
a processing unit including a processor and in communication with or part of one or more of the visual image system, the thermal image system, and the location mapping system,
wherein the location mapping system generates a map of the working space of the area, and
wherein the processing unit overlays the visual image, the thermal image, the information from the location mapping system to identify an animate object, locate the animate object, and track the animate object within the working space of the area.

2. The system of claim 1, wherein the location mapping system automatically generates a geofence that defines the working space.

3. The system of claim 2, wherein the geofence is dynamically adjusted in response to movement of the one or more of the inanimate objects within the area.

4. The system of claim 1, wherein the location mapping system determines a percentage of the area that is attributed to the working space and a percentage of the area that is attributed to the one or more blind zones.

5. The system of claim 1, wherein the thermal image system detects a thermal signature of an object positioned within the working space.

6. The system of claim 5, wherein the visual image system and the thermal image system cooperate to identify the object as an object of interest, and wherein the location mapping system is configured to determine a location of the object within the working space on the map, and wherein the map is defined by an X-Y map generated by the location mapping system.

7. The system of claim 6, wherein the working space includes a first workspace zone and a second workspace zone.

8. The system of claim 6, wherein, when the object of interest is in or enters a blind zone of the area, the system is configured to predict a next position of the object within the area.

9. The object detection and tracking system of claim 1, wherein one or more of the visual image system, the thermal image system, and the location mapping system directly process the visual image, the thermal image, or the location information, respectively.

* * * * *